United States Patent
Matsunaga et al.

(10) Patent No.: US 8,357,530 B2
(45) Date of Patent: Jan. 22, 2013

(54) MICROFLUIDIC DEVICE FOR TRAPPING SINGLE CELL

(75) Inventors: Tadashi Matsunaga, Tokyo (JP); Atsushi Arakaki, Tokyo (JP); Tomoyuki Taguchi, Tokyo (JP); Masahito Hosokawa, Tokyo (JP)

(73) Assignee: National University Corporation Tokyo University of Agriculture and Technology, Tokyo (JP)

(*) Notice: Subject to any disclaimer, the term of this patent is extended or adjusted under 35 U.S.C. 154(b) by 301 days.

(21) Appl. No.: 12/670,990

(22) PCT Filed: Jul. 31, 2008

(86) PCT No.: PCT/JP2008/002058
§ 371 (c)(1),
(2), (4) Date: Apr. 30, 2010

(87) PCT Pub. No.: WO2009/016842
PCT Pub. Date: Feb. 5, 2009

(65) Prior Publication Data
US 2010/0240041 A1    Sep. 23, 2010

(30) Foreign Application Priority Data
Aug. 1, 2007 (JP) .................... 2007-201373

(51) Int. Cl.
*C12N 5/00* (2006.01)
*C12N 5/02* (2006.01)
(52) U.S. Cl. ........................ 435/325; 435/395

(58) Field of Classification Search .......... 435/325, 435/395
See application file for complete search history.

(56) References Cited

U.S. PATENT DOCUMENTS
2004/0259238 A1* 12/2004 Bashir et al. ............. 435/287.1

FOREIGN PATENT DOCUMENTS

| JP | 10-332688 | 12/1998 |
|---|---|---|
| JP | 2002-27969 | 1/2002 |
| JP | 2004-000144 | 1/2004 |
| JP | 2006-42654 | 2/2006 |
| JP | 2006-191877 | 7/2006 |
| JP | 2006-280231 | 10/2006 |
| JP | 2006-345868 | 12/2006 |
| JP | 2007-43903 | 2/2007 |
| JP | 2007-89566 | 4/2007 |

OTHER PUBLICATIONS

Chiou et al., "Massively Parallel Manipulation of Single Cells and Microparticles Using Optical Images," Nature, 436, p. 370-372, Jul. 21, 2005.
Yamamura et al., "Single-Cell Microarray for Analyzing Cellular Response," Anal. Chem., 77, pp. 8050-8056, 2005.
Carlo et al., "Single-Cell Enzyme Concentrations, Kinetics, and Inhibition Analysis Using High-Density Hydrodynamic Cell Isolation Arrays," Anal. Chem., 78, pp. 4925-4930, 2006.

* cited by examiner

*Primary Examiner* — Robert T. Crow
(74) *Attorney, Agent, or Firm* — Kenneth H. Sonnenfeld; Margaret B. Brivanlou; King & Spalding (57) ABSTRACT

The instant invention is directed to a microfluidic device which separates and captures with high efficiency a large amount of cells in a sample at one-cell level without damaging the cells by utilizing a microfabrication technology.

10 Claims, 6 Drawing Sheets

Target: Hematopoietic stem cells; HSCs)
⇒ Rare cells present in peripheral blood mononuclear cells at the rate of about 0.1%.

1. Loading of human peripheral blood mononuclear cells (PBMCs)

PBMCs : 10⁴ cells    Microfluidic device    10000-hole micromesh

2. Detection and separation of single HSC cells

Cell separation by micro capillary 3. mRNA-expression analysis of single HSC cells → 4. Single cell RT-PCR

MICROFLUIDIC DEVICE FOR TRAPPING SINGLE CELL

TECHNICAL FIELD

The present invention relates to a microfluidic device for capturing a single cell, that can capture cells contained in a sample at one-cell level; a method for separating and capturing cells contained in a sample at one-cell level using the microfluidic device; and a method for quantitatively analyzing a gene expression of a single cell utilizing the microfluidic device.

BACKGROUND ART

Heretofore, since an effective means for capturing a single cell has not yet been established, a global competition is underway. There are papers on a massively parallel manipulation of single cells with optoelectronic tweezers (for example, see non-patent document 1), single-cell microassay by a polystylene microchamber array chip (for example, see non-patent document 2), and a separation of a single cell by a high-density hydrodynamic cell-isolation array (for example, see non-patent document 3), as well as patent documents related to a device or a method for capturing cells as stated below.

For example, a slide for separating cells enabling a gene analysis by separating cells using existing instruments in a general blood test room without needing a skill, wherein the cell separation is enabled by attaching the cells to the slide and then cutting off the part to which one or more cells have been attached (for example, see patent document 1); and a kit for diagnosing cancer, infectious disease, or other pathological process, comprising a selectively-activatable transport surface which can be activated so as to provide a selective region having an adhesive property, and at least one probe or marker that can be applied to a cellular material sample from an abnormal tissue so as to distinguish a cellular material sample from a normal tissue and the cell sample from the abnormal tissue, are known (for example, see patent document 2).

Furthermore, a device for separating and sorting cells, that can produce a large number of cell-containing drops with a small diameter while preventing damages to the cells, which device comprises a cell-alignment part in which a cell suspension containing a large number of cells are treated to make the cells align and then flow at an interval; a cell information detection part which detects information on the cells by subjecting the cells aligned in the cell-alignment part to a detection process; and a cell-sorting part which sorts out cells based on the information detected at the cell information detection part, wherein the cell-alignment part is provided with a first passage for flowing the cell suspension, and a second passage which communicates with the first passage in the direction crossing the first passage, which second passage is for flowing a fluid substance for interrupting the cell-suspension flow of the first passage; and a substrate for aligning cells, are known (for example, see patent document 3).

Further, a method for separating cells, comprising the steps of: allowing a target cell to take in via a transporter a specific substance for labeling and distinguishing; optically detecting a substance labeled with the specific substance for labeling and distinguishing that has been taken in, to separate the target cell; and separating the specific substance for labeling and distinguishing taken in by the separated target cell, wherein a cell is labeled, and a target cell is subjected to an electrolytic force and then separated and recovered using a cell separation device for separating the cell from other cells, in a manner so as to minimize the impact on the cell and to facilitate the utilization of the recovered cell, is known (for example, see patent document 4).

Further, a cell capturing device which enables an easy and reliable cell-capture and transmission observation of cells, wherein a cell petri-dish of the cell capturing device has a structure in which a pair of through-pores at two positions of a bottom-plate part and an intake-channel linking the lower openings of the through-pores are formed, a transparent plate member is provided to seal a groove part from the lower side of the bottom-plate part, a capture plate is arranged at the positions of upper openings of the through-pores, and a suction tube leading from a suction pump is connected to the upper openings of the through-pores, is known (for example, see patent document 5).

Further, a micro-channel array device that can solve various problems in the actual use of microinjection method, that facilitates a capture of a particle and an insertion of a needle while observing a cell under a microscope and that can efficiently inject a substance to the particle (for example, to a cell), which device consists of a first substrate having on its surface a concave that has a though-pore penetrating the substrate and a number of micro grooves that communicate between the concave and an end face of the substrate, and a transparent second substrate, wherein the second substrate is joined to the surface of the first substrate, whereby an open end for capturing a particle, constituted by the groove, is formed on the end face of the first substrate which is a part joining the first substrate and the second substrate, is known (for example, see patent document 6).

Meanwhile, the present inventors have reported a device for separating a microorganism, capable of separating and recovering a subject microorganism selectively and accurately from sample water, comprising a flat plate substrate having a flow channel including a fluid-supply opening and a fluid-suction opening formed inside; a microchip provided at the fluid-suction opening of the flat plate substrate, having a capture part consisting of a plurality of through-pores with a diameter smaller than the minimum diameter of the subject microorganism; a water-sample suction means connected to the capture part of the microchip to suction the water sample; and a sample-water supply means connected to the fluid-supply opening of the flat plate substrate of the microchip to supply the sample water, in the device for separating a microorganism that separates and recovers the subject microorganism contained in the sample water (for example, see patent document 7).

Patent Document 1: Japanese Laid-Open Patent Application No. 10-332688
Patent Document 2: Japanese Laid-Open Patent Application No. 2006-345868
Patent Document 3: Japanese Laid-Open Patent Application No. 2004-144
Patent Document 4: Japanese Laid-Open Patent Application No. 2006-42654
Patent Document 5: Japanese Laid-Open Patent Application No. 2006-280231
Patent Document 6: Japanese Laid-Open Patent Application No. 2002-27969
Patent Document 7: Japanese Laid-Open Patent Application No. 2007-89566
Non-patent Document 1: Pei Yu Chiou, Aaron T. Ohta, Ming C. Wu, All, Nature Vol. 436, 21 Jul. 2005, p 370
Non-patent Document 2: Shohei Yamamura et al., Anal. Chem., 2005, Vol. 77, p 8050-8056

Non-patent Document 3: Dino Di Cario, Nima Aghdam, Luke P. Lee, Anal. Chem. 2006, Vol. 78, p 4925-4930

DISCLOSURE OF THE INVENTION

Object to be Solved by the Invention

In recent years, abnormal clones of immune cells in pathologies such as cancer or autoimmune diseases have attracted attention. Considering the dynamic adaptation mechanism of immunity, it is readily conceived that individual cells have different functional characteristics. From the viewpoint of immune response also, the mutation of TCRs or antibody-genes is a phenomenon starting from one cell at the beginning, and in this era, it is no longer possible to avoid studying at one-cell level, in a function-study of an immune cell. As stated, the target of a cell analysis is increasingly broken down from a group of cells to a single cell, and further to an intracellular molecule. In a single cell analysis, a high speed and exhaustive capture as well as a batch analysis of the cells are desired. The object to be attained by the present invention is to provide a microfluidic device that separates and captures (traps) a large amount of cells in a sample with high efficiency at a single-cell level without damaging the cells using a microfabrication technology.

Means to Solve the Object

The present inventors previously proposed a device for separating a microorganism that separates and recovers a subject microorganism contained in sample water (see patent document 7). This device for separating a microorganism comprises a microchip consisting of a 5 μm-thick SUS 304 thin plate provided with a plurality of through-pores having a mortar-like shape, and microorganisms such as pseudo particles of Cryptosporidium can be captured efficiently using this device. However, a trial was made to separate and capture cells in a sample at one-cell level using this device for separating a microorganism, to reveal that it was difficult to separate and capture cells at one-cell level without damaging the cells, that the cells adsorbed within the flow channels including the fluid-supply opening and the fluid-suction opening, and moreover, that the device did not permit an adequate observation of a cell surface and was inconvenient for a preparative isolation of the separated and captured cells.

Figure 1:
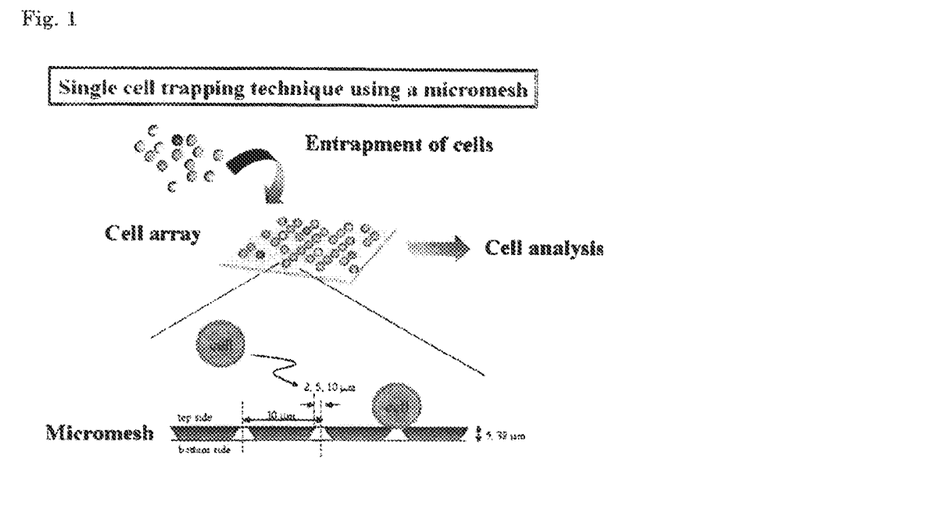
FIG. 1 This is a pattern diagram of a cell array and a micromesh.

Consequently, a study on the material of a micromesh, a study on the shape of a micro though-pore for capturing a cell of the micromesh, a study on the surfactant for preventing cell adsorption within the microchannel, a study on the material and structure of constituent members of the microfluidic device, and a study on the suction pressure were performed. As a result, a microfluidic device was constructed by processing micro pores having an inverted mortar-like shape with 2 μm diameter, arranged in a 100-pore array on a PET (polyethylene terephthalate) substrate to produce a PET micromesh (see FIG. 1), integrating the PET micromesh with a microchannel formed by two PDMS (polydimethylsiloxane) flat plates that have different hardness, and treating the inner surface of the microchannel with a nonionic surfactant (see FIG. 2). A Raj i-cell suspension was introduced into the channel to suction (vacuum) and capture the cells on the micromesh, and it was found that cells can be captured with higher efficiency as compared to a conventional device, with the maximum rate of about 80%, and that the captured cells can be arrayed at regular intervals. After capturing cells, the present inventors further conducted a membrane permeabilization for introducing a FISH probe, subsequently introduced a fluorescently-labeled probe targeting at human β-actin mRNA into the channel, performed a FISH staining, then measured the fluorescence intensity of the cells, and assessed quantitatively the expression level of human β-actin mRNA in individual cells. Consequently, it was found that the changes in the expression level of human β-actin mRNA in the cells cultured under a serum-fed condition and a serum-starved condition can be revealed at a single-cell level. The present invention has thus been completed based on the findings stated above.

More specifically, the present invention relates to [1] a microfluidic device capable of capturing animal cells contained in a sample at one-cell level by a micromesh, comprising sequentially an upper substrate consisting of a plastic flat plate wherein a sample-supply opening and a sample-discharge opening are formed on a surface and a groove for forming a microchannel communicating the sample-supply opening and the sample-discharge opening is provided on a lower surface; a plastic upper flat plate forming the microchannel by cooperating with the upper substrate, the plate being provided with an aperture for a micromesh at a position corresponding to a part of the microchannel; a micromesh-holding flat plate consisting of a plastic micromesh having a plurality of micro through-pores for capturing cells at a position corresponding to a downward side of the aperture of the upper flat plate, and a holding plate holding the micromesh; and a plastic lower flat plate provided with an aperture for suctioning at a position corresponding to a downward side of the micromesh of the holding flat plate; and a lower substrate consisting of a plastic flat plate wherein a suction opening is formed on a surface and a groove for forming a suction channel which communicates the aperture for suctioning and the suction opening by cooperating with the lower flat plate is provided on an upper surface; wherein the micro through-pores for capturing cells of the micromesh have an inverted mortar-like shape or a cylindrical shape, the upper flat plate is constituted by a softer plastic as compared to the upper substrate, and the upper substrate and the upper flat plate, or the upper flat plate and the micromesh-holding flat plate are mountably and dismountably constructed.

The present invention further relates to [2] the microfluidic device according to [1], wherein the micromesh is made of a material with low intrinsic fluorescence; [3] the microfluidic device according to [1] or [2], wherein one side of the lower substrate is provided with a step part having an equal height to a sequence of the lower flat plate, micromesh-holding plate, upper flat plate, and upper substrate that are layered from the bottom, so as to constitute the lower flat plate, micromesh-holding flat plate, upper flat plate and upper substrate stably layered and mounted on a lower substrate at the time of reduced-pressure suctioning; [4] the microfluidic device according to any one of [1] to [3], wherein the upper substrate and the upper flat plate are made of plastic comprising PDMS (poly-dimethylsiloxane) as a main agent; [5] the microfluidic device according to any one of [1] to [4], wherein an inner surface of the microchannel is treated with a nonionic surfactant; [6] the microfluidic device according to [5], wherein the nonionic surfactant is a polyoxyethylene.polyoxypropylene block copolymer-type nonionic surfactant; [7] the microfluidic device according to any one of [1] to [6], wherein the holding plate holding the micromesh is made of glass; and [8] the microfluidic device according to any one of [1] to [7], wherein the micromesh is made of PET and has inverted mortar-like shaped micro through-pores for capturing cells; the upper substrate and the upper flat plate are made of plastic comprising PDMS as a main agent; the holding plate holding the micromesh is made of glass; the inner surface of a microchannel formed by a cooperation of the upper substrate and the upper flat plate, has been treated with a nonionic surfactant; and wherein a cell-capture rate is at least 50%.

The present invention further relates to [9] a method for capturing cells contained in a sample at one-cell level, comprising injecting a sample containing animal cells from the sample-supply opening of the microfluidic device according to any one of [1] to [8], and suctioning at a suction pressure of −10 kPa to −0.1 kPa; and [10] a method for quantitatively analyzing a gene expression of a single cell, comprising capturing animal cells contained in a sample at one-cell level using the microfluidic device according to any one of [1] to [8], introducing a fluorescent probe to each of captured cells, and subsequently measuring a fluorescence intensity of the single cell by a fluorescence excitation.

BEST MODE OF CARRYING OUT THE INVENTION

The microfluidic device of the present invention is not particularly limited as long as it is a microfluidic device capable of capturing cells contained in a sample at one-cell level by a micromesh, comprising sequentially an upper substrate consisting of a plastic flat plate wherein a sample-supply opening and a sample-discharge opening are formed on a surface and a groove for forming a microchannel communicating the sample-supply opening and the sample-discharge opening is provided on a lower surface; a plastic upper flat plate forming the microchannel by cooperating with the upper substrate, the plate being provided with an aperture for a micromesh at a position corresponding to a part of the microchannel; a micromesh-holding flat plate consisting of a plastic micromesh having a plurality of micro through-pores for capturing cells at a position corresponding to a downward side of the aperture of the upper flat plate, and a holding plate holding the micromesh; and a plastic lower flat plate provided with an aperture for suctioning at a position corresponding to a downward side of the micromesh of the holding flat plate; and a lower substrate consisting of a plastic flat plate wherein a suction opening is formed on a surface and a groove for forming a suction channel which communicates the aperture for suctioning and the suction opening by cooperating with the lower flat plate is provided on an upper surface; wherein the micro through-pores for capturing cells of the micromesh have an inverted mortar-like shape or a cylindrical shape, the upper flat plate is constituted by a softer plastic as compared to the upper substrate, and the upper substrate and the upper flat plate, or the upper flat plate and the micromesh-holding flat plate are mountably and dismountably constructed. A device with a cell capture rate of at least 50%, in particular, at least 60%, is preferred. Further, as for the above cell, an animal cell such as a human cell, a cell of a mammal other than human, and an insect cell can be preferably exemplified, and an immune cell such as a T cell and B cell are particularly preferably exemplified. These cells may be modified, altered, or labeled in advance. Further, a sample containing these cells is not particularly limited as long as it is a fluid sample, which may be, for example, blood, lymph, cultured-cell suspension, or somatic-cell suspension, while a sample containing at least 100 to 100000 cells is preferred so as to gain sufficient benefit from the effect of the microfluidic device of the present invention.

The upper substrate is not particularly limited as long as it is a plastic flat plate wherein a sample-supply opening and a sample-sending opening are formed on the surface (the upper surface or sides) and a groove for forming a microchannel communicating the sample-supply opening and the sample-sending opening is provided on the lower surface. The upper surface may be somewhat curved, and the lower surface may be somewhat curved as long as the lower surface can be layered liquid-tightly with the upper surface of the upper flat plate. However, a flat plate with the upper and the lower surfaces both having a level surface is preferred in terms of a simple processing. As for a groove for forming a microchannel, a groove to form a curved inner surface, such as a groove with a semi-cylindrical shaped (semicircular in cross-section) inner surface, or a square groove which is rectangular in cross section, can be preferably exemplified in terms of preventing cell attachment. Usually, a sample-supply means such as a sample-supply pump is connected through a sample-supply line to supply a sample to the sample-supply opening. Further, on the sample-supply line upstream of the sample-supply pump, a sample-supply valve and a sample storage tank can be connected sequentially from the upstream side towards the downstream side. Further, a sample-sending means such as a sample-sending pump may be connected to the sample-sending opening through a sample-sending line, while a sample-sending valve may be simply fixed. As for the sample-supply pump and the sample-sending pump, a micro pump capable of controlling a microflow, such as a tube pump or a plunger pump can be specifically exemplified.

The upper flat plate is not particularly limited as long as it is a plastic upper flat plate forming the microchannel by cooperating with the upper substrate, the plate being provided with an aperture for a micromesh at a position corresponding to a part of the microchannel. Since the upper flat plate forms the microchannel by cooperating with the upper substrate, it is possible to provide a groove for forming a microchannel, for example, a groove with a semi-cylindrical shaped (semi-circular in cross-section) inner surface, on the upper surface at the position corresponding to the groove for forming a microchannel provided on the upper substrate, while it is also possible to form a microchannel with a flat upper surface. Further, an aperture for a micromesh is preferably of a size which allows an exposure of the whole surface of the micromesh. As for the shape of the aperture, a circular shape or a rectangular shape such as a square shape can be specifically exemplified.

The micromesh-holding flat plate is not particularly limited as long as it is a flat plate holding a plastic micromesh having a plurality of inverted mortar-like shaped or cylindrical micro through-pores for capturing cells, and is constituted by a micromesh and a holding plate having a micromesh-holding opening which is slightly smaller than the micromesh. When the micro through-pores have a mortar-like shape, they may not be able to separate and capture cells at one-cell level, while making the micro through-pores into an inverted mortar-like shape or cylindrical shape enables a reliable separation and capture of cells at one-cell level. The diameter of the upper end opening of the micro through-pore is slightly smaller than the diameter of a cell to be captured, and can be 2 to 10 µm. Further, the number of the micro through-pores is 100 to 100000, and preferably 1000 to 10000. Further, the cell-capture efficiency can be improved by setting the center-to-center distance between the micro through-pores to be 30 to 70 µm, preferably 40 to 60 µm, and more preferably 50 µm. Therefore, a micromesh comprising 100000 micro through-pores is about 0.8 cm×2 cm in size.

Further, it is required that the material for a micromesh is a plastic. When the micromesh is made of a metal such as SUS, it is difficult to process micro through-pores into a uniform size and shape (an inverted mortar-like shape or a cylindrical shape) consistently in a case where the upper-end opening diameter of the pore is 2 µm or smaller. Different from a case where the capture target is a microorganism, a suction condition of mildly reduced pressure is applied to a case where the target is a cell. Therefore, a micromesh can be made of plastic which is less resistant to suction pressure but inexpensive and has a good formability that permits an easy formation of micro through-pores of a uniform size and shape. Among those plastics, material with transparency and low intrinsic fluorescence is preferred. The transparency allows an observation of a cell surface. Specifically, plastics such as PET, PMMA, PC, COP, and epoxy can be exemplified, while PET is preferred because it shows less heat deformation by laser processing and provides high processing accuracy. Further, it is possible to use advantageously a colored plastic which is black, dark brown, dark blue or the like for the purpose of reducing intrinsic background fluorescence, and for example, black PET can be preferably exemplified.

The plastic lower flat plate is not particularly limited as long as it is a flat plate provided with an aperture for suctioning at the position corresponding to the downward side of the micromesh of the micromesh-holding flat plate, which can form a suction channel by cooperating with the lower substrate. The shape of the aperture for suctioning, too, is not particularly limited, but it is usually constituted as a circular shape. The lower flat plate is constituted as a flat-plate shape that can keep airtight the gap between the micromesh-holding flat plate and the lower substrate under a suction condition of a reduced pressure.

The lower substrate is not particularly limited as long as it consists of a plastic flat plate wherein a suction opening is formed on the surface and a groove for forming a suction channel which communicates the aperture for suctioning and the suction opening by cooperating with the lower flat plate is provided on the upper surface. The suction opening is coupled to the reduced-pressure suction means, and the sample solution on a micromesh is discharged by sequentially passing micro through-pores, aperture for suctioning, suction channel and suction opening, at which time, the cells are captured one by one by the upper-end opening part of the micro through-pores. At the time of the suction, the sample-sending valve in the downstream of the sample-sending opening of the upper substrate may be blocked. Further, one side of the lower substrate is preferably provided with a step part having an equal height to a sequence of the lower flat plate, micromesh-holding plate, upper flat plate, and upper substrate that are layered from the bottom. By providing such a step part, the lower flat plate, micromesh-holding flat plate, upper flat plate and upper substrate can be stably layered and mounted on a lower substrate at the time of reduced-pressure suctioning, and these flat plates can be held securely by a suction pressure without fixing them to each other with a bolt or the like. In an opposite manner, these flat plates can be detached from each other easily when the reduced pressured is released.

The preferred material for the upper substrate, upper flat plate, lower flat plate, and lower substrate is hard plastics, and they can be of the same material or different materials without particular limitation. They can be exemplified by plastic flat plates made of PDMS, PMMA, PC, hard polyethylene and the like, while PDMS is preferred in terms of the close contact to the micromesh-holding flat plate. Further, as for the material for a micromesh-holding flat plate, the above-mentioned plastics and the like can be exemplified apart from glass, while glass (glass slide) is preferred in terms of the close contact and the sticking workability with the plastic flat plate.

Moreover, as mentioned above, the present invention is characterized in that the upper flat plate is constituted by a softer plastic as compared to the upper substrate. Under a suction condition of a highly reduced pressure, an upper flat plate provided with an aperture for a micromesh and a micromesh-holding flat plate made of a glass slide contact closely, and therefore a sample solution can be sent without leaking. However, because animal cells are captured under a suction condition of mildly reduced pressure, use of an upper flat plate as hard as an upper substrate may cause a problem in the close contact between them, which leads to leaking of the sample solution. Therefore, constituting the upper flat plate by a softer plastic as compared to the upper substrate enhances the adhesion (close contact) between the upper flat substrate, upper flat plate, and the holding plate holding the micromesh, thereby leaking of the sample solution can be prevented. For example, an upper flat plate constituted by a softer material as compared to an upper substrate can be produced by formulating a hardener to be mixed with PDMS which is the main agent, at a rate of 1/10 to 1/2, preferably 1/5 to 1/3 as compared to the upper substrate. As stated above, use of an upper flat plate constituted by a softer material as compared to an upper substrate enhances the liquid-tightness between the upper substrate, upper flat plate and holding plate holding a micromesh, and consequently, a solution-sending operation can be performed without causing leaking even under a suction condition of mildly reduced pressure. Moreover, before and after capturing cells, at least the upper substrate and the upper flat plate, or the upper flat plate and the micromesh-holding flat plate can be easily mounted or dismounted, thereby captured cells can be easily picked up or observed microscopically. Further, the lower surface of the upper substrate and the upper surface of the upper flat plate can be can be treated with plasma and allowed to adhere in advance by immediately sticking them together after the plasma treatment.

Likewise, constituting the lower flat plate by a softer plastic as compared to the lower substrate enhances the adhesion (close contact) between the lower substrate, lower flat plate, and the holding plate holding a micromesh, thereby leaking of the sample solution can be prevented. As seen from the above, the soft plastic in the present invention is a plastic with a consistency that enhances the adhesion (close contact) to a holding plate holding a micromesh during a suction under a reduced pressure, thereby able to prevent leaking of the sample solution. For example, a lower flat plate constituted by a softer material as compared to a lower substrate can be produced by formulating a hardener to be mixed with PDMS which is the main agent, at a rate of 1/10 to 1/2, preferably 1/5 to 1/3 as compared to the lower substrate. As stated above, use of a lower flat plate constituted by a softer material as compared to a lower substrate can enhance the liquid-tightness between the lower substrate, lower flat plate and holding plate holding a micromesh, and consequently a suction operation can be performed without leaking even under a suction condition of mildly reduced pressure. Further, the upper surface of the lower substrate and the lower surface of the lower flat plate can be treated with plasma and allowed to adhere in advance by immediately sticking them together after the plasma treatment.

In order to prevent a cell from attaching to the inner surface of a microchannel, it is preferable to treat in advance with a nonionic surfactant the inner surface of a microchannel formed by a cooperation of the upper substrate and the upper flat plate, and preferably the upper surface of a micromesh in addition to the inner surface of the microchannel. It is more preferable to perform a surface plasma treatment prior to the treatment with a nonionic surfactant. By coating the surface using an anionic surfactant, it is possible to prevent the adsorption of a microorganism with a negatively-charged surface potential. However, this does not sufficiently prevent the adsorption of a cell, and therefore the cell has to be treated with a nonionic surfactant. As for the nonionic surfactant, a block polymer-type ether, polyoxyethylene hardened caster oil, sucrose fatty acid ester (sugar ester), polyoxyethylene sorbitan fatty acid ester, and sucrose fatty acid ester can be exemplified, while a block polymer-type ether, in particular a polyoxyethylene polyoxypropylene block copolymer-type nonionic surfactant, is preferred. Examples of the above block polymer-type ether include polyoxyethylene (196) polyoxypropylene (67) glycol (Pluronic F127), polyoxyethylene (160) polyoxypropylene (30) glycol (Pluronic F68), polyoxyethylene (42) polyoxypropylene (67) glycol (Pluronic P123), and polyoxyethyleneoxypropylene cetyl ether (20E. O4P. O). Examples of the polyoxyethylene hardened caster oil include a hydrogenated caster oil polyoxyethylene ether and polyoxyethylene hydrogenated caster oil. Examples of the polyoxyethylene sorbitan fatty acid ester include Polysorbate (Tween 40), Polysorbate 60 (Tween 60), Polysorbate 65, Polysorbate 80 (Tween 80), and polyoxyethylene sorbitan monolaurate (20E. O). For example, when a polyoxyethylene polyoxypropylene block copolymer-type nonionic surfactant such as Pluronic F127 is used, the concentration thereof is 0.5 to 10%, and preferably about 1 to 5%.

The method for capturing cells contained in a sample at one-cell level of the present invention is not particularly limited as long as it is a method comprising injecting a sample containing cells from a sample-supply opening of the above-mentioned microfluidic device of the present invention and suctioning at a suction pressure of −10 kPa to −0.1 kPa, and preferably at −5 kPa to −1 kPa. Suctioning at a suction pressure higher than −10 kPa (pressure difference greater than 10 kPa), for example, the suction pressure of −20 kPa, will destroy a cell and a suction pressure lower than −0.1 kPa (pressure difference smaller than 0.1 kPa) will reduce the capture efficiency.

The analysis method of the present invention is not particularly limited as long as it is a FISH method or the like comprising capturing cells contained in a sample at one-cell level using the above microfluidic device of the present invention, introducing a fluorescent probe into each cell that has been captured, and then quantitatively analyzing gene expression of a single cell by a fluorescence excitation. More specifically, a quantitative analysis of gene expression of a single cell is enabled by allowing the microfluidic device to capture cells one by one, then introducing a 50% ethanol/PBS into a microchannel, setting the microfluidic device on a hot plate to permeabilize the cells, introducing into the permeabilized cells a fluorescently labeled oligonucleotide probe such as a Cy3-labeled oligonucleotide probe for a specific gene mRNA for them to hybridize, and measuring the fluorescence intensity of the individual single cells.

Further, by using the microfluidic device of the present invention, T-cells or B-cells contained in a sample can be separated and captured at one-cell level, which enables an analysis and identification of a functional T-cell receptor (TCR) at the level of a single T-cell that expresses on the cell membrane a TCR recognizing a cancer-specific antigen peptide, and an analysis and identification of a functional antibody at the level of a single B-cell that expresses on the cell membrane an antibody recognizing a cancer-specific antigen peptide, thereby an immune response can be monitored. In this manner, by analyzing and identifying the gene of a cancer-specific TCR and antibody from a patient with cancer, information can be obtained on the whole picture of the types of the cancer antigen-specific TCR and antibody produced in an individual patient, thereby a tailor made-like diagnosis of an individual patient becomes possible.

Hereinbelow, the present invention will be described more specifically with reference to the examples, while the technical scope of the present invention will not be limited to these exemplifications.

(Construction of microfluidic device)

A mold for producing a microchannel (depth: 1 mm, width: 1 mm) was made by cutting a 3 mm-thick PMMA (polymethylmethacrylate) substrate using CAD-CAMM (computer-aided design-computer-aided modeling machine system; PNC-300, Roland Corporation). This mold was ultrasonically cleaned and then dried. PDMS (poly-dimethylsiloxane) which is the main agent and a hardener (Sylgard 184; Dow Corning Co.) were mixed at 10:1. The mixture was poured into the mold and then deaerated under a reduced pressure to produce an upper substrate. Further, an upper flat plate provided with an aperture for a micromesh was produced by using a mixture formulated with PDMS and a hardener at 50:1. The PDMS was hardened by heating at 85° C. for 20 minutes or more. The surfaces were treated with plasma for 20 seconds. Immediately after the plasma treatment, the PDMSs were allowed to adhere by sticking them together to produce a microchannel member. Further, a silicone tube (inner diameter 1 mm×outer diameter 3 mm) was connected to a sample-supply opening and a sample-sending opening. Likewise, PDMS and a hardener were mixed at 10:1, and the mixture was poured into a mold and then deaerated under a reduced pressure to produce a lower substrate. Further, a mixture formulated with a main agent and a hardener at 50:1 was used for a lower flat plate. The PDMS was hardened by heating at 85° C. for 20 minutes or more. The surfaces were treated with plasma for 20 seconds. Immediately after the plasma treatment, the PDMSs were allowed to adhere by sticking them together to produce a suction channel member. Further, a silicone tube was connected to a suction opening.

A 38 μm-thick black bPET (black polyethylene terephthalate; Muranaka Medical Instruments Co., Ltd.) was used to produce a micromesh. Each micro through-pore has an inverted mortar-like shape, and was designed so that the diameter of the pore is 2 μm at the smaller side of the pore. Further, a total of 100 pores in a 10×10 distribution with a 30-μm center-to-center distance, a total of 1250 pores in a 25×50 distribution with a 60-μm center-to-center distance, and a total of 10000 pores in a 100×100 distribution with a 60-μm center-to-center distance were arranged in an array form, respectively. Based on this design, a photomask was produced from a glass substrate with vapor-deposited chrome. By using this mask, micro through-pores were processed onto the bPET substrate with the use of a laser of 248 nm in wavelength and 150 Hz in frequency by Excimer laser micromachine (Optec Micro-Master System, Optec). This bPET substrate was adhered using an epoxy bonding agent to a glass slide where a through-pore having a 10 mm-diameter had been made, to produce a micromesh-holding flat plate. Finally, the micromesh-holding flat plate was tucked between the microchannel member and the suction channel member to construct a microfluidic device.

(Preliminary Experiment; Study on the Suction Pressure)

Figure 2:
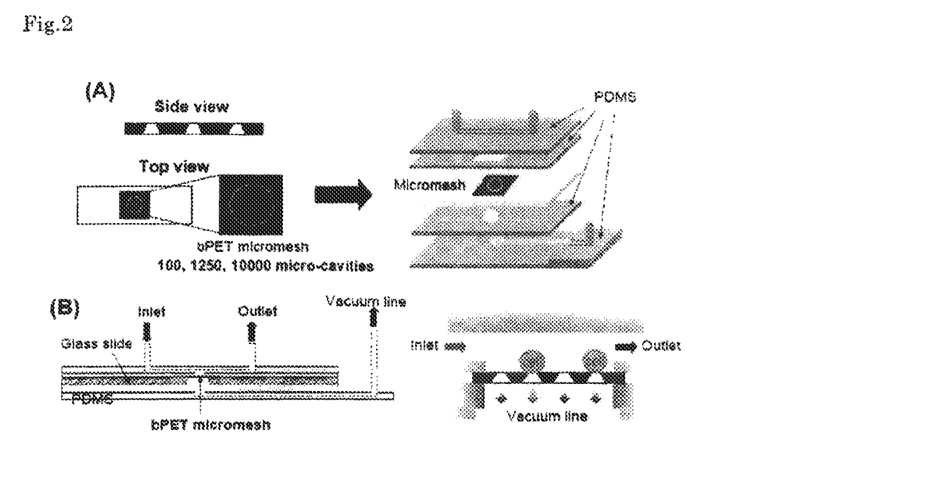
FIG. 2 This is a pattern diagram of the microfluidic device of the present invention. "A" shows an assembly drawing and "B" shows a longitudinal sectional view.
Figure 3:
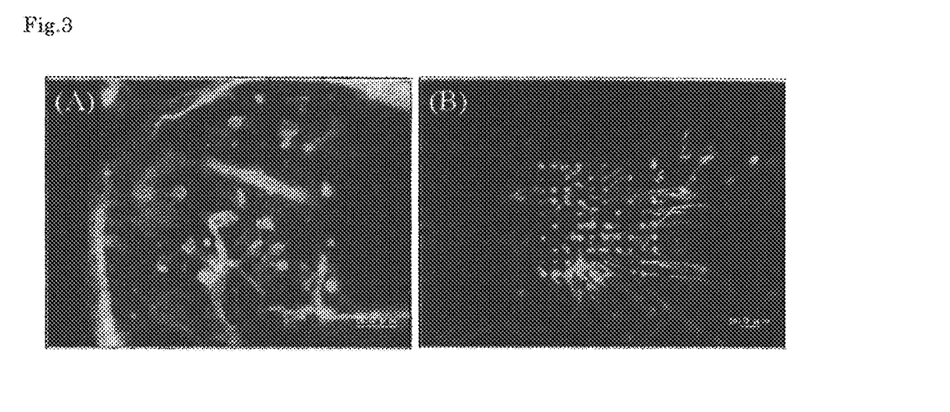
FIG. 3 These are pictures showing the results of a study of the suction pressure in cell capture. These are fluorescence micrographs of Raji cells captured on a SUS micromesh at a pressure difference of 90 kPa (−90 kPa). "A" shows the upper surface and "B" shows the lower surface. The Raji cells were stained with DAPI and observed with a WU filter set (ex.: 330-385, em.: 420<). A scale bar of 50 μm is used.
Figure 4:
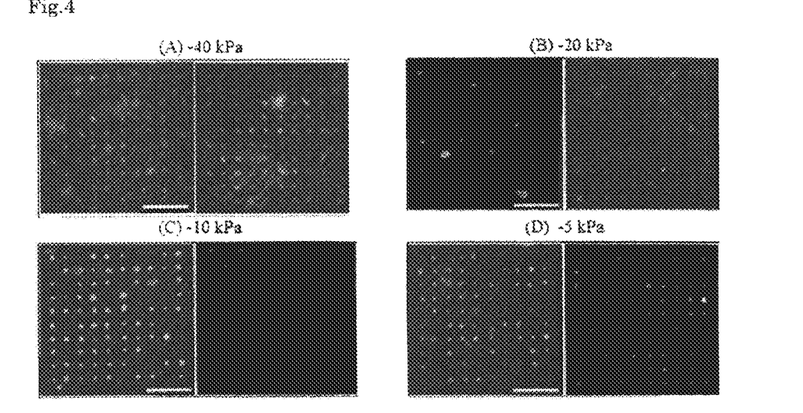
FIG. 4 These are pictures showing the results of a study of the suction pressure in cell capture. These are fluorescence micrographs of Raji cells captured on a SUS micromesh. The pressure difference was 40 kPa (−40 kPa) in "A"; 20 kPa (−20 kPa) in "B"; 10 kPa (−10 kPa) in "C"; and 5 kPa (−5 kPa) in "D". Left side images show upper surfaces and right side images show lower surfaces. The Raji cells were stained with DAPI and observed with a WU filter set (ex.: 330-385, em.: 420<). A scale bar of 100 μm is used.

A study was made on a suction pressure in a cell capture using Raji cells (human Burkitt lymphoma) as test cells with the use of the microfluidic device shown in FIG. 2 except that the device comprises a micromesh consisting of a 5 μm-thick SUS 304 thin plate instead of a 38 μm-thick black PET (bPET), as a method to avoid damages to the cells. As a result, unlike the case of a microorganism, in the case of a cell, the cell was destroyed at the pressure difference of 90 kPa (−90 kPa) as shown in FIG. 3. Therefore, a study was made on a suction pressure in a cell capture in a similar manner by changing the suction pressure to −40 kPa (pressure difference of 40 kPa), −kPa (pressure difference of 20 kPa), −10 kPa (pressure difference of 10 kPa), and −5 kPa (pressure difference of 5 kPa). The results are shown in FIG. 4. Consequently, it was found that a cell can be captured efficiently under the suction condition of mildly reduced pressure of −5 kPa.

(Study on the Material for Micromesh)

Figure 5:
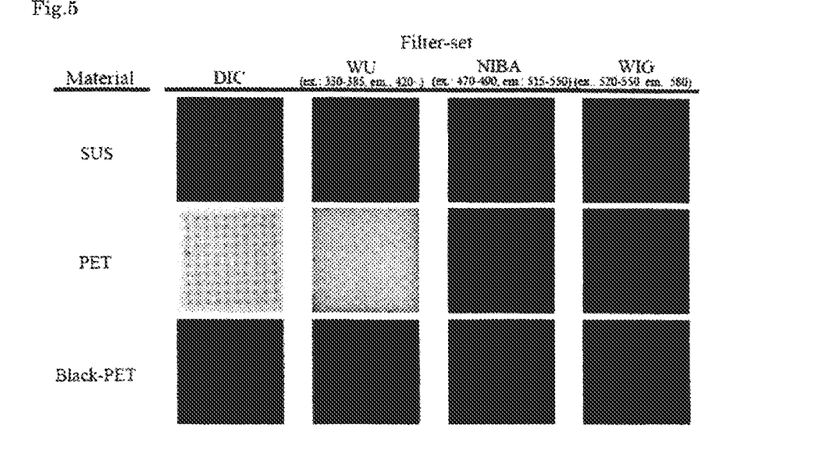
FIG. 5 This is a figure showing the results of a study of the material for a micromesh.

Intrinsic background fluorescence was examined using a 5 μm-thick SUS 304 thin plate, a 5 μm-thick PET film (Muranaka Medical Instruments Co., Ltd.) and a 38 μm-thick black PET film (Muranaka Medical Instruments Co., Ltd.) as materials for a micromesh. The results are shown in FIG. 5. Consequently, it was found that a SUS and semitransparent black PET emit less intrinsic fluorescence than a transparent PET.

(Observation of the Shape of Micro Through-Pores in Pet Micromesh and SUS Micromesh)

Figure 6:
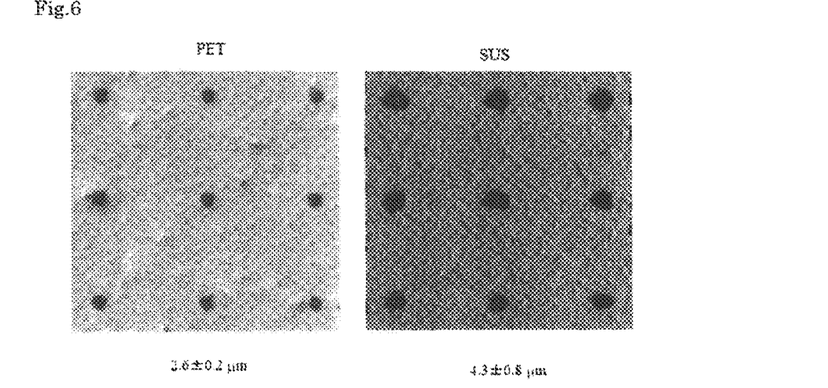
FIG. 6 These are pictures showing the shape of micro through-pores on a PET micromesh and a SUS micromesh.
Figure 7:
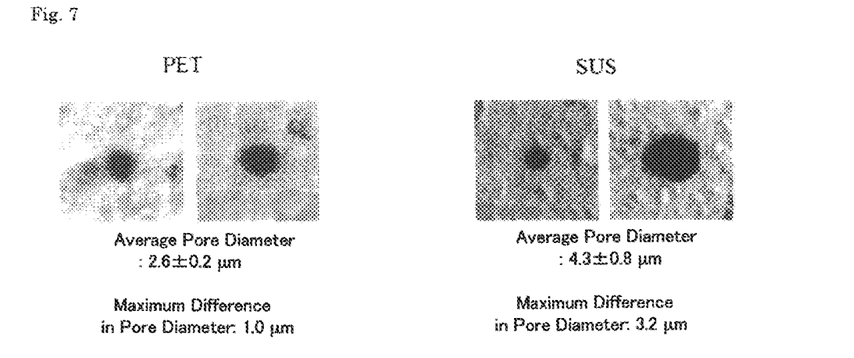
FIG. 7 These are pictures showing the shape of micro through-pores on a PET micromesh and a SUS micromesh.
Figure 8:
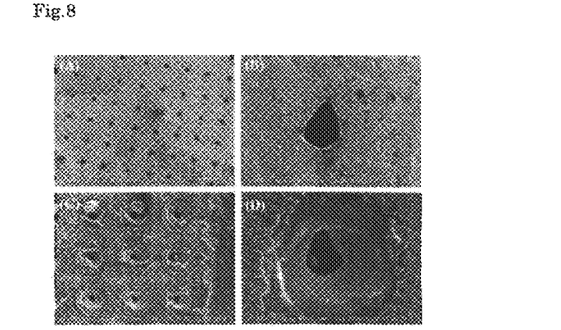
FIG. 8 These are pictures showing scanning electron microscopic (SEM) images of a SUS micromesh. "A" and "B" show upper surfaces and "C" and "D" show lower surfaces.

The shapes of micro through-pores having an inverted mortar-like shape were examined in a PET micromesh and SUS micromesh. Scanning electron microscopic (SEM) images are shown in FIG. 6 to FIG. 8. It was found from FIG. 6 to FIG. 8 that more uniform and accurate micro processing is possible with PET than with SUS.

(Cell Capture Efficiency)

Figure 9:
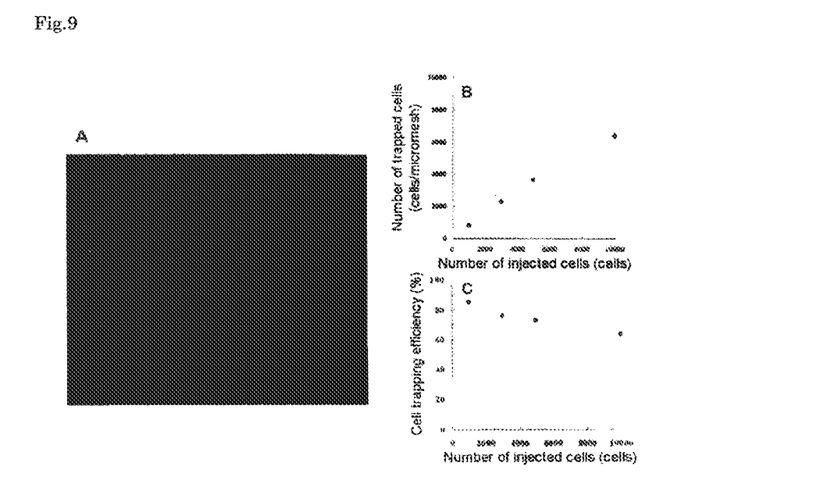
FIG. 9 This is a figure showing a cell-capture efficiency under a suction condition of a pressure difference of 1.5 kPa (−1.5 kPa), on a black PET micromesh having 10000 micro through-pores. "A" shows a scanning image, "B" shows the number of cells captured on the micromesh, and "C" shows the capture efficiency.

1000, 3000, 5000, and 10000 Raji cells were injected under the suction condition of 1.5 kPa pressure difference (−1.5 kPa) into a microfluidic device mounted with a black PET micromesh having 10000 micro through-pores, and the number of cells captured on the micromesh was measured with a scanner. The scanning image, the number of cells captured on the micromesh, and the capture efficiency are shown in FIG. 9. As can be seen from FIG. 9, the cell capture efficiency of 60% or more can be achieved by using the microfluidic device of the present invention.

(Viability of the Captured Cell)

1000 Raji cells stained with Calcein-AM were examined for their viability under the suction condition of 1.5 kPa pressure difference (−1.5 kPa) before and after the cells were captured by the microfluidic device mounted with a black PET micromesh. A PI solution was introduced and the Calcein-AM-stained Raji cells before and after capturing were observed on fluorescence micrographs (synthetic images) using an NIBA filter set (ex.: 470-490, em.: 515-550) and WIG filter set (ex.: 520-550, em.: 580). According to the results, the cell viability before capturing was 96.8% while the cell viability after capturing was 91.3%. Therefore, the viability of the captured cells according to the method for capturing cells of the present invention can be rated as distinctly high.

(Prevention of Cell Attachment to PDMS Microchannel by Nonionic Surfactant)

Figure 10:
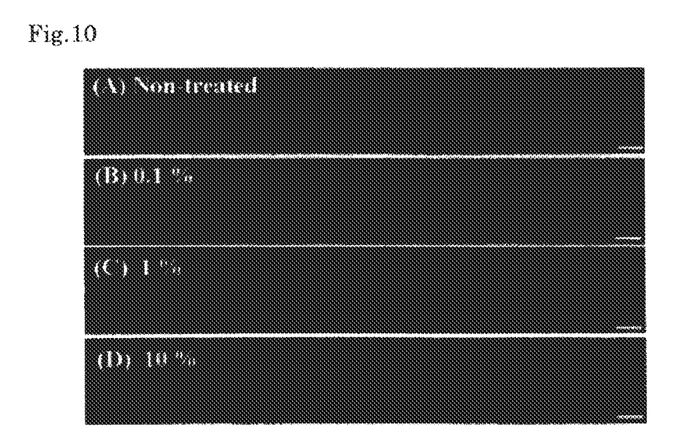
FIG. 10 This is a figure showing fluorescence micrographs of Raji cells attached to the inner surface of a microchannel treated with a nonionic surfactant (Pluronic F127). 1500 Raji cells stained with Cell Tracker Red CMTPX were introduced into a PDMS microchannel and observed with a WIG filter set (ex.: 520-550, em.: 580).

The microchannel of the microfluidic device comprising a PDMS microchannel member was treated with a nonionic surfactant (Pluronic F127) at the concentrations of 0.1%, 1%, and 10%, respectively. Subsequently, 1500 Raji cells stained with CellTracker Red CMTPX were injected and the Raji cells attached to the inner surface of the microchannel were observed on fluorescence micrographs with a WIG filter set (ex.: 520-550, em.: 580). The results are shown in FIG. 10. It was found that a treatment with a 1% Pluronic F127 solution can prevent cells from attaching to the PDMS microchannel.
(Quantitative Analysis of Gene Expression of a Single Cell by Fluorescence Excitation)

Figure 11:
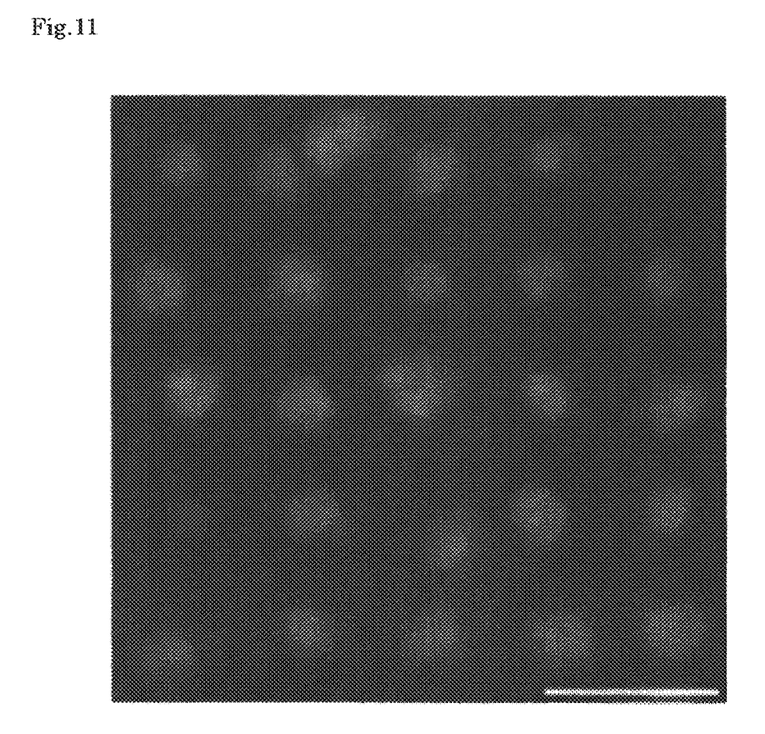
FIG. 11 This is a figure showing a fluorescence micrograph of a captured Raji cell detected by FISH.
Figure 12:
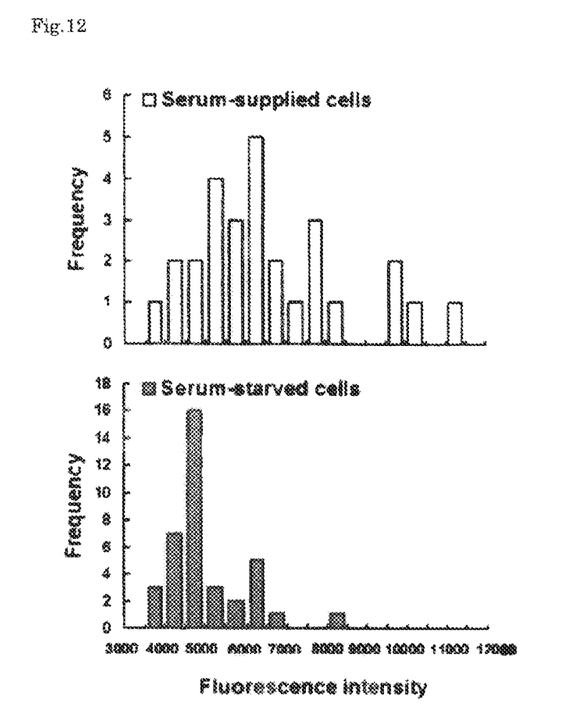
FIG. 12 This is a figure showing histograms of the fluorescence intensity of captured Raji cells detected by FISH.

A microfluidic device mounted with a black PET micromesh was used to capture Raj i cells. Subsequently, a 50% ethanol/PBS was introduced into a microchannel. The microfluidic device was then set on a hot plate to permeabilize the cells. Cy3-labeled oligonucleotide probes for human β-actin were used for the hybridization with the permeabilized cells at 42° C. for 2 hours. The fluorescence micrographs are shown in FIG. 11. Further, a mixed suspension of Calcein-AM-labeled serum-starved Raji cells (n=38) and serum-treated Raji cells (n=28) was introduced into the microfluidic device and the cells were captured on a black PET micromesh. Subsequently, FISH was performed on the microfluidic device for human β-actin mRNA, using Cy3-labeled oligonucleotide probes for human β-actin mRNA. Next, the fluorescence intensity of a single cell was measured. The results are shown in FIG. 12. The fluorescence intensity of the cells with enhanced expression of human β-actin mRNA due to the serum treatment was greater than that of the serum-starved cells with suppressed expression of human β-actin mRNA. It is found from the foregoing that a quantitative analysis of gene expression of a single cell is possible by using the microfluidic device.
(Separation and Capture of CTL at One-Cell Level by Microfluidic Device)

For the purpose of isolating only cells co-expressing CD8 which is a CTL marker and an antigen receptor for a gp100 peptide, a suspension of CTL cells treated by double-fluorescence immunostaining using FITC-labeled anti-CD8 antibody+/PE-labeled gp100-HLA-A2-tetramer was introduced into the microfluidic device, and suctioned at a reduced pressure of −2.0 kPa to capture cells on a black PET micromesh. An observation of the cells on the black PET micromesh using a fluorescence microscope (BX-51; Olympus) confirmed that the cells were successfully separated and captured at one-cell level.
(Separation and Capture of Rare Cell by Microfluidic Device)

Figure 13:
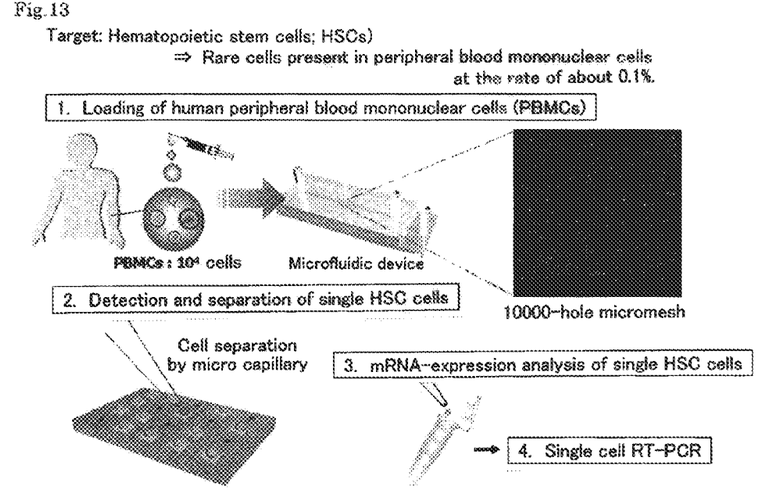
FIG. 13 This is a pattern diagram showing a separation of hematopoietic cells (HSCs) from human peripheral blood mononuclear cells (PBMCs) using the 10000-hole microfluidic device of the present invention.
Figure 14:
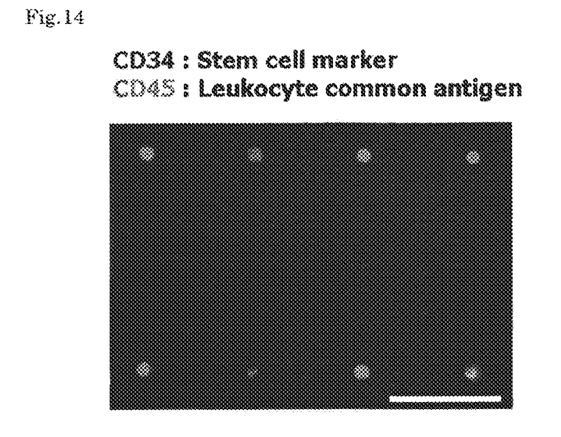
FIG. 14 This is a figure showing the detection results of CD34+ cells on the 10000-hole microfluidic device of the present invention. In the photograph, a cell expressing CD34 which is a stem-cell marker is shown in red in the lower row at one point which is the first from the right, and CD45s which are leukocyte common antigens are shown in green in the upper row at all four points and in the lower row at three points which are the first to third from the left. A scale bar of 60 μm is used.
Figure 15:
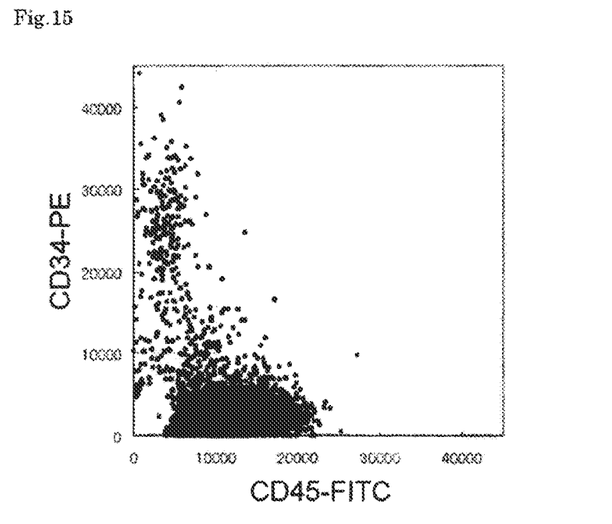
FIG. 15 This is a figure showing the correlation of fluorescence intensities between PE and FITC. Each dot shows the fluorescence intensity of a single cell. Single cells were stained with FITC-labeled anti-CD45 antibodies and PE-labeled anti-CD34 antibodies.

An outline of the separation and capture of hematopoietic stem cells (HSCs) that are rare cells present at the rate of about 0.1% in human peripheral-blood mononuclear cells (PBMCs) using the microfluidic device is shown in FIG. 13. $10^4$ PBMCs subjected to a double-fluorescence immunostaining using FITC-labeled anti-CD45 antibodies and PE-labeled anti-CD34 antibodies were captured by a microfluidic device mounted with a 10000-hole black PET micromesh, and then observed under a fluorescence microscope with a power-operable stage arranged, using an NIBA and WIG filter sets to obtain a fluorescence image of the entirety of the micromesh. This fluorescence micrograph is shown in FIG. 14. The photograph shows CD45$^+$ cells stained in green (in the upper row at all four points and in the lower row at three points that are the first to third from the left) and CD34% cells stained in red (in the lower row at one point which is the first from the right). Further, the correlation between the fluorescence intensities of PE and FITC among $10^4$ PBMCs treated by double-fluorescence immunostaining is shown in FIG. 15.

Consequently, HSC cells that are present at the rate of only about 0.1% in PBMCs were successfully captured at one-cell basis by using the micromesh according to the present invention, at an extremely high rate of 90% or more of the 10000 holes, thereby it was confirmed that even a very rare cell (the cell stained in red) can be recovered reliably without a loss. As stated, when the microfluidic device of the present invention is used, a multistaining of cells using an immunostaining method can be utilized for a profiling analysis of cells contained in peripheral blood. Further, it was found that an ultrasensitive detection of a target cell is possible by using a plastic containing a pigment as a substrate material.
(Single Cell Separation by Capillary)

From among the group of cells captured on the micromesh as state above, only red-stained CD34$^+$ cells (HSC cells) were separated manually with a capillary and picked. Further, as a control, only CD45$^+$ cells were separated manually with a capillary and picked. Then, the picked CD34$^+$ cells and CD45$^+$ cells were used as samples to perform RT-PCR. A reverse transcription reaction was performed under the conditions of 60 minutes at 42° C., and PCR was performed 50 cycles each under the respective conditions of 30 seconds at 94° C., 30 seconds at 60° C., and 30 seconds at 72° C. The amplified products were electrophoresed to analyze mRNA expressed intracellularly.

Figure 16:
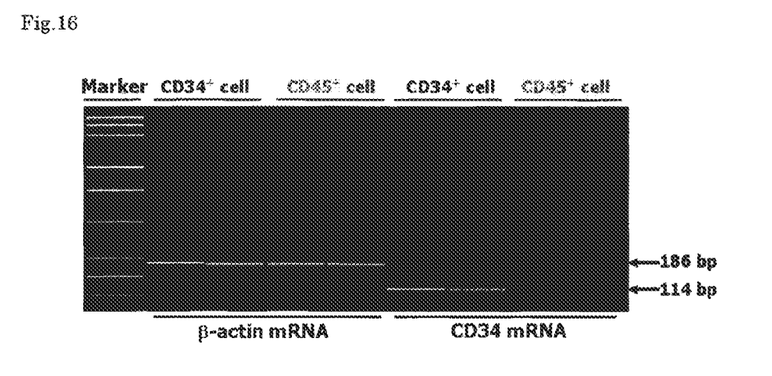
FIG. 16 This is a figure showing the results of a mRNA expression analysis of a single cell using RT-PCR. An analysis was performed on CD34 mRNA expressed in single cells (CD34$^+$ cells and CD45$^+$ cells) separated form PBMCs captured with a 10000-hole black PET micromesh. A β actin mRNA expression was also analyzed as a control experiment.

The results of CD34 mRNA and β-actin mRNA expressions based on the mRNA expression analysis of a single cell using the RT-PCR is shown in FIG. 16.

Consequently, because the cells captured on the micromesh can be exposed on the surface as they are by removing the plastic upper flat plate, and can be recovered as single cells from the exposed group of cells with a capillary, it was found that cells can be served undamaged as samples for an expression analysis, and further, that the association between a cell and the nucleic acids expressed therein can be directly examined relatively easily by analyzing the samples that have been separated as individual cells.

INDUSTRIAL APPLICABILITY

It has been revealed that, by using the microfluidic device of the present invention, a large amount of cells in a sample can be reliably separated and captured at one-cell level at a high rate of 80% without damaging the cells; that a target cell can be ultrasensitively detected by using a plastic containing a pigment as a substrate material, in particular; that the association between a cell and the nucleic acids expressed therein can be directly examined relatively easily by analyzing the sample that have been separated into individual cells; and that the cells captured on the micromesh can be exposed on the surface while staying in the same state, by simply removing the plastic upper flat plate (being made of adhesive material, the plastic upper flat plate can be attached and detached) and can be recovered with a capillary, thereby the cells can be served undamaged as samples for an expression analysis. For example, a visualization and quantitative analysis of mRNA in a single cell is enabled by capturing cells contained in a sample at one-cell level, introducing a fluorescent probe into each captured cell, and then quantitatively analyzing gene expression of a single cell by a fluorescence excitation, i.e., FISH (Fluorescence in situ hybridization). Further, seen from the viewpoint of tumor-immunology, an immune-response monitoring is enabled because a functional T-cell receptor (TCR) can be analyzed and identified at a single T-cell level, which has conventionally been considered impossible.

Moreover, the microfluidic device of the present invention facilitates the introduction of various reagents by the solution-sending, and therefore is an optimum tool for a cell analysis by a real-time observation. The device of the present invention thus is a promising research-support tool that can be utilized for analyzing the mechanism of a target-cell induction and for culturing a target cell, in the area of stem cells and the like including iPS cells that are currently a focus of attention.

The invention claimed is:

1. A microfluidic device capable of capturing animal cells contained in a sample at one-cell level by a plastic micromesh, comprising sequentially an upper substrate consisting of a plastic flat plate wherein a sample-supply opening and a sample-discharge opening are formed on a surface and a groove for forming a microchannel communicating the sample-supply opening and the sample-discharge opening is provided on a lower surface;

a plastic upper flat plate forming the microchannel by cooperating with the upper substrate, the plastic upper flat plate being provided with an aperture for a plastic micromesh at a position corresponding to a part of the microchannel;

a micromesh-holding flat plate consisting of the plastic micromesh having a plurality of micro through-pores for capturing cells at a position corresponding to a downward side of the aperture of the plastic upper flat plate, and a holding plate holding the plastic micromesh;

a plastic lower flat plate provided with an aperture for suctioning at a position corresponding to a downward side of the plastic micromesh of the micromesh-holding flat plate; and a lower substrate consisting of a plastic flat plate wherein a suction opening is formed on a surface and a groove for forming a suction channel which communicates the aperture for suctioning and the suction opening by cooperating with the plastic lower flat plate is provided on an upper surface;

wherein the micro through-pores for capturing cells of the plastic micromesh have an inverted mortar-like shape or a cylindrical shape, the plastic upper flat plate is constituted by a softer plastic as compared to the upper substrate, and the upper substrate and the plastic upper flat plate, or the plastic upper flat plate and the micromesh-holding flat plate are mountably and dismountably constructed.

2. The microfluidic device according to claim 1, wherein the plastic micromesh is made of a material with less intrinsic fluorescence than a transparent PET (polyethylene terephthalate).

3. The microfluidic device according to claim 1, wherein one side of the lower substrate is provided with a step part having an equal height to a sequence of the plastic lower flat plate, the micromesh-holding flat plate, the plastic upper flat plate, and the upper substrate that are layered from the bottom, so as to constitute the plastic lower flat plate, the micromesh-holding flat plate, the plastic upper flat plate and the upper substrate stably layered and mounted on the lower substrate at a time of reduced-pressure suctioning.

4. The microfluidic device according to claims 1, wherein the upper substrate and the plastic upper flat plate are made of plastic comprising PDMS (poly-dimethylsiloxane) as a main agent.

5. The microfluidic device according to claims 1, wherein an inner surface of the microchannel is treated with a nonionic surfactant.

6. The microfluidic device according to claim 5, wherein the nonionic surfactant is a polyoxyethylene.polyoxypropylene block copolymer-type nonionic surfactant.

7. The microfluidic device according to claims 1, wherein the micromesh-holding plate holding the plastic micromesh is made of glass.

8. The microfluidic device according to claims 1, wherein the plastic micromesh is made of PET and has inverted mortar-like shaped micro through-pores for capturing cells;

the upper substrate and the plastic upper flat plate are made of plastic comprising PDMS as a main agent;

the micromesh-holding plate holding the plastic micromesh is made of glass;

the inner surface of a microchannel formed by a cooperation of the upper substrate and the plastic upper flat plate has been treated with a nonionic surfactant; and wherein a cell-capture rate is at least 50%.

9. A method for capturing cells contained in a sample at one-cell level, comprising injecting a sample containing animal cells from the sample-supply opening of the microfluidic device according to any one of claims 1 to 8, and suctioning at a suction pressure of −10 kPa to −0.1 kPa.

10. A method for quantitatively analyzing a gene expression of a single cell, comprising capturing animal cells contained in a sample at one-cell level using the microfluidic device according to any one of claims 1 to 8, introducing a fluorescent probe to each of the captured cells, and subsequently measuring a fluorescence intensity of the single cell by a fluorescence excitation.

* * * * *

UNITED STATES PATENT AND TRADEMARK OFFICE
CERTIFICATE OF CORRECTION

PATENT NO. : 8,357,530 B2
APPLICATION NO. : 12/670990
DATED : January 22, 2013
INVENTOR(S) : Tadashi Matsunaga et al.

It is certified that error appears in the above-identified patent and that said Letters Patent is hereby corrected as shown below:

In the Claims

Column 16, claim 4, line 8, the term "claims" should read --claim--.

Column 16, claim 5, line 12, the term "claims" should read --claim--.

Column 16, claim 6, lines 16-17, the term "polyoxyethylene.polyoxypropylene" should read --polyoxyethylene·polyoxypropylene--.

Column 16, claim 7, line 18, the term "claims" should read --claim--.

Column 16, claim 8, line 21, the term "claims" should read --claim--.

Signed and Sealed this
Fourth Day of June, 2013

Teresa Stanek Rea
*Acting Director of the United States Patent and Trademark Office*